US008014956B2

(12) United States Patent
Chang et al.

(10) Patent No.: US 8,014,956 B2
(45) Date of Patent: Sep. 6, 2011

(54) MICRORNA PRECURSORS

(75) Inventors: Yu-Ching Chang, Hsinchu County (TW); Yu-Yu Lin, Yilan County (TW); Shiu-Chieh Lan, Taichung (TW); Cheng-Tao Wu, Taipei County (TW); Chung-Cheng Liu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 1245 days.

(21) Appl. No.: 11/617,042

(22) Filed: Dec. 28, 2006

(65) Prior Publication Data

US 2007/0218479 A1 Sep. 20, 2007

Related U.S. Application Data

(60) Provisional application No. 60/755,427, filed on Dec. 30, 2005.

(51) Int. Cl.
*G06F 7/00* (2006.01)
(52) U.S. Cl. ............... 702/19; 702/20; 703/11; 707/700; 536/24.1
(58) Field of Classification Search ........................ None
See application file for complete search history.

(56) References Cited

U.S. PATENT DOCUMENTS

| 2005/0075492 A1 | 4/2005 | Chen et al. |
| 2005/0142581 A1 | 6/2005 | Griffey et al. |
| 2005/0186589 A1 | 8/2005 | Kowalik et al. |
| 2005/0266552 A1 | 12/2005 | Doench et al. |
| 2005/0272923 A1 | 12/2005 | Zhang et al. |
| 2007/0042380 A1 | 2/2007 | Bentwich et al. |

FOREIGN PATENT DOCUMENTS

| WO | WO 2004/048511 | 6/2004 |
| WO | WO 2004/066183 | 8/2004 |
| WO | WO 2005/017111 | 2/2005 |
| WO | WO 2005/111211 | 11/2005 |

OTHER PUBLICATIONS

Altschul et al., "Basic Local Alignment Search Tool," *J. Mol Biol.*, 215(3): 403-410 (1990).
Altschul et al., "Gapped BLAST and PSI-BLAST: a new generation of protein database search programs," *Nucleic Acids Res.*, 25(17): 3389-3402 (1997).
Bartel, "MicroRNAs: Genomics, Biogenesis, Mechanism, and Function," *Cell*, 116(2): 281-297 (2004).
Benson, "Tandem repeats finder: a program to analyze DNA sequences," *Nucleic Acids Res.*, 27(2): 573-580 (1999).
Berezikov et al., "Phylogenetic Shadowing and Computational Identification of Human microRNA Genes," *Cell*, 120(1): 21-24 (2005).
Bonnet et al., "Evidence that microRNA precursors, unlike other non-coding RNAs, have lower folding free energies than random sequences," *Bioinformatics*, 20(17): 2911-2917 (2004).
Chang et al., "Explore MicroRNA Precursors through a High-Throughput Computational Prediction," The Seventeenth International Conference on Genome Informatics, Poster and Software Demonstrations, P106-1~P106-2, Yokohama, Japan, Dec. 2006.
Cheng et al., "Association of Liver Tumor Function with a Novel Predicted Candidate MicroRNA," Industrial Technology Research Institute Biotechnology Forum, Hsinchu, Taiwan, Nov. 2006.
Grad et al., "Computational and Experimental Identification of *C. elegans* microRNAs," *Mol Cell.*, 11(5): 1253-1263 (2003).
Griffiths-Jones, "The microRNA Registry," *Nucleic Acids Res.*, 32 D109-111 (2004).
Hofacker et al., Fast Folding and Comparison of RNA Secondary Structures (The Vienna RNA Package), *Monatsh Chem.*, 125: 167-188 (1994).
Kim, "MicroRNA Biogenesis: Coordinated Cropping and Dicing," *Nat Rev Mol. Cell Biol.*, 6(5): 376-385 (2005).
Lagos-Quintana et al., "Identification of Novel Genes Coding for Small Expressed RNAs," *Science*, 294(5543): 853-858 (2001).
Lagos-Quintana et al., "Identification of Tissue-Specific MicroRNAs from Mouse," *Curr Biol.*, 12(9): 735-739 (2002).
Lagos-Quintana et al., "New microRNAs from mouse and human," *RNA*, 9(2): 175-179 (2003).
Lau et al., "An Abundant Class of Tiny RNAs with Probable Regulatory Roles in *Caenorhabditis elegans*," *Science*, 294(5543): 858-862 (2001).
Lee et al., "An Extensive Class of Small RNAs in *Caenorhabditis elegans*," *Science*, 294(5543): 862-864 (2001).
Lim et al., "Vertebrate MicroRNA Genes," *Science*, 299(5612): 1540 (2003).
Lim et al., "The microRNAs of *Caenorhabditis elegans*," *Genes Dev.*, 17(8):991-1008 (2003).
Lim et al., "Microarray analysis shows that some microRNAs downregulate large numbers of target mRNAs," *Nature*, 433(7027): 769-773 (2005).
Nam et al., "Human microRNA prediction through a probabilistic co-learning model of sequence and structure," *Nucleic Acids Res.*, 33(11): 3570-3581 (2005).
Rhoades et al., "Prediction of Plant MicroRNA Targets," *Cell*, 110: 513-520 (2002).
Tanzer et al., "Molecular Evolution of a MicroRNA Cluster," *J Mol Biol.*, 339: 327-335 (2004).
Wang et al., "MicroRNA identification based on sequence and structure alignment," *Bioinformatics*, 21(18): 3610-3614 (2005).
Workman et al., "No evidence that mRNAs have lower folding free energies than random sequences with the same dinucleotide distribution," *Nucleic Acids Res.*, 27: 4816-4822 (1999).
Xie et al., "Systematic discovery of regulatory motifs in human promoters and 3' UTRs by comparison of several mammals," *Nature*, 434(7031): 338-345 (2005).
Xue et al., "Classification of real and pseudo MicroRNA precursors using local structure-sequence features and support vector machine," *BMC Bioinformatics*, 6:310 (2005).
Yang et al., "SVM-based Identification of microRNA precursors," Proceedings of 4th Asia-Pacific Bioinformatics Conference, 267-276, Taipei, Taiwan, Feb. 2006.
Yu et al, "Feature Selection for High-Dimensional Data: A Fast Correlation-Based Filter Solution," Proceedings of the Twentieth International Conference on Machine Leaning (ICML-03), 856-863 (2003).

*Primary Examiner* — Mary Zeman
(74) *Attorney, Agent, or Firm* — Finnegan, Henderson, Farabow, Garrett & Dunner, LLP (57) ABSTRACT

Disclosed are methods of identifying microRNA motifs or microRNA precursors for a target gene or a set of target genes. Also disclosed are related computer-readable media.

17 Claims, 2 Drawing Sheets

MICRORNA PRECURSORS

RELATED APPLICATION

This application claims priority to U.S. application Ser. No. 60/755,427, filed Dec. 30, 2005, the contents of which are incorporated herein by reference.

BACKGROUND

MicroRNAs (miRNAs) are a group of endogenous ~21-23 nt noncoding RNAs. The regulate expression of genes at the postranscriptional level (Bartel, 2004 Cell, 116(2):281-97). Although only recently discovered, they have been found to play key roles in a wide variety of biological processes, including cell fate specification, cell death, cell proliferation, and fat storage. So far, more than 300 different human miR-NAs have been identified (Griffiths-Hones, 2004, Nucleic Acids Res. 32 D109-111). Most of them are though to recognize their mRNA targets via partial antisense complementarity. This partial complementarity, as well as the short lengths of miRNAs and their targets, makes identification of novel miRNAs difficult by conventional sequence comparison methods. Thus, there is a need for a novel approach for identifying miRNAs and their targets.

SUMMARY

This invention is based on the development of a computational method for predicting miRNAs and their targets.

In one aspect, this invention features of identifying a microRNA motif for a set of target genes. The method includes (a) providing a set of subject nucleic acid sequences that contain coding regions (CDRs), 5' untranslated regions (5'UTRs), and 3' untranslated regions (3'UTRs) of the target genes; and (b) determining the $DIFF_{CDRs}$ or $DIFF_{5'UTRs}$ value of a test RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad \text{(I) and}$$

$$DIFF_{5'UTRs} = g(OBS_{3'UTRs}, OBS_{5'UTRs}, EXP_{3'UTRs}, EXP_{5'UTRs}) \quad \text{(II)}$$

In the above functions, $DIFF_{CDRs}$ and $DIFF_{5'UTRs}$ represent the degrees of the enrichment of the test motif in all of the 3' untranslated regions in comparison with all of the coding regions and all of the 5' untranslated regions, respectively; $OBS_{3'UTRs}$, $OBS_{CDRs}$, and $OBS_{5'UTRs}$ represent the observed counts of the test motif within all of the 3' untranslated regions, all of the coding regions, and all of the 5' untranslated regions, respectively; and $EXP_{3'UTRs}$, $EXP_{CDRs}$, and $EXP_{5'UTRs}$ represent the expected counts of the test motif within all of the 3' untranslated regions, all of the coding region, and all of the 5' untranslated region, respectively. The two functions mentioned above can take the form of Formula III and IV below:

$$DIFF_{CDRs} = \frac{OBS_{3'UTRs} - OBS_{CDRs}}{MAX(EXP_{3'UTRs}, EXP_{CDRs})} \quad \text{(III)}$$

and $$DIFF_{5'UTRs} = \frac{OBS_{3'UTRs} - OBS_{5'UTRs}}{MAX(EXP_{3'UTRs}, EXP_{5'UTRs})}. \quad \text{(IV)}$$

The test motif can be a contiguous RNA segment containing 5 to 11 nucleotides. The set of target genes can be expressed in a pre-determined biological sample, which can be prepared from a tissue (e.g., a brain tissue or a liver tissue) or a cell culture (e.g., a HepG2 cell culture). In one embodiment, the set of target genes is determined from the microarray expression profiles provided by the Genomics Institute of the Novartis Research Foundation.

This invention also features a method of identifying a microRNA motif for a target gene. The method includes (a) providing a subject nucleic acid sequence that contains coding regions (CDRs), 5' untranslated regions (5'UTRs), and 3' untranslated regions (3' UTRs) of the target gene; and (b) determining the $DIFF_{CDRs}$ or $DIFF_{5'UTRs}$ value of a test RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad \text{(V) and}$$

$$DIFF_{5'UTRs} = g(OBS_{3'UTRs}, OBS_{5'UTRs}, EXP_{3'UTRs}, EXP_{5'UTRs}) \quad \text{(VI)}$$

$DIFF_{CDRs}$ and $DIFF_{5'UTRs}$ represent the degrees of the enrichment of the test motif in all of the 3' untranslated regions in comparison with all of the coding regions and all of the 5' untranslated regions, respectively; $OBS_{3'UTRs}$, $OBS_{CDRs}$, and $OBS_{5'UTRs}$ represent the observed counts of the test motif within all of the 3' untranslated regions, all of the coding regions, and all of the 5' untranslated regions, respectively; and $EXP_{3'UTRs}$, $EXP_{CDRs}$, and $EXP_{5'UTRs}$ represent the expected counts of the test motif within all of the 3' untranslated regions, all of the coding regions, and all of the 5' untranslated regions, respectively. The set of functions can take the form of Formula VII and VIII below:

$$DIFF_{CDRs} = \frac{OBS_{3'UTRs} - OBS_{CDRs}}{MAX(EXP_{3'UTRs}, EXP_{CDRs})} \quad \text{(VII)}$$

and $$DIFF_{5'UTRs} = \frac{OBS_{3'UTRs} - OBS_{5'UTRs}}{MAX(EXP_{3'UTRs}, EXP_{5'UTRs})}. \quad \text{(VIII)}$$

The test motif can be a contiguous segment containing 5 to 11 nucleotides.

In another aspect, the invention features a method for identifying a microRNA precursor. The method includes:

(a) providing a subject DNA sequence;

(b) searching, by a heuristic algorithm, in the subject DNA sequence of step (a) for a DNA region that has a strong tendency to form a stem loop;

(c) retaining a DNA region of step (b) that does not reside in a low complexity region of the subject DNA sequence;

(d) assessing the ability of the retained DNA region of step (c) to fold into a secondary structure, and selecting a DNA region whose corresponding RNA sequence has a low energy of folding and forms a stem loop;

(e) comparing the energy of folding of two selected DNA regions of step (d) that overlap with each other substantially such that both overlap ratios exceed a predetermined value, and choosing the one with the lowest energy of folding;

(f) assessing the stability of a chosen DNA region of step (e) by performing randomized shuffle of the chosen DNA region a number of times, while keeping a characteristic property of the chosen DNA region unchanged, and calculating a score as a measure of the stability of the secondary structure formed by the chosen DNA region;

and (g) identifying, from one or more chosen DNA regions, a target section that has a stability score higher than a predetermined value. The target section is determined to be a microRNA precursor. The subject DNA sequence can contain a genomic DNA sequence, a such as genomic DNA sequence from a metazoan species (e.g., *Homo Sapiens*).

The low complexity region in step (c) can be a region of biased composition including homo-polymeric runs, short-period repeats, or subtler overrepresentation of one or more nucleotides. Various web-based sequence alignment servers (such as BLAST server) can be used for filtering the results against such regions since they tend to generate spurious results that reflect compositional bias rather than significant alignments. Genomic DNA sequences with low complexity regions masked out by tools such as RepeatMasker or Tandem Repeat Finder (G. Benson, Nucleic Acids Res., 1999, 27, 573-580) are available for download. The energy of folding in step (d) can be calculated with an RNA secondary structure prediction tool, e.g., Vienna RNA package (Hofacker et al., 1994, Monatsh. Chem., 125, 167-188). Preferably, the low energy of folding in step (d) is no greater than −18 kcal/mol, e.g., no greater than −20 kcal/mol, −21 kcal/mol, −22 kcal/mol, −23 kcal/mol, −24 kcal/mol, or −25 kcal/mol. The phrase "overlap with each other substantially" refers to that the overlap ratio of the two DNA regions exceeds a predetermined value. For example, an overlap ratio of two regions $R_A$=[nt100, nt200] and region $R_B$=[nt110, nt220] can be calculated as 90% according to the formula $$\frac{\text{overlaping\_length}}{\min(\text{RA\_length, RB\_length})} = \frac{90}{\min(100, 110)} = 90\%.$$

The characteristic property of the DNA region in step (f) can be a mono-nucleotide distribution or a di-nucleotide distribution.

The above-mentioned heuristic algorithm can further include (1) selecting a pair of seeds (i.e., two contiguous segments, each having a length of 3 to 8 nucleotides) that are spaced within a pre-determined distance, wherein the bases of the seeds match to each other according to a base pairing rule (e.g., matching Watson-Crick complementary base pairs (A-T, T-A, C-G, and G-C) or matching non-canonical G-T wobble base pairs (G-T and T-G)); and (2) extending, from the pair of seeds, the DNA region in the direction toward and away from each other using an extension rule, and stopping the extension upon the fulfillment of a criterion. The extension in step (2) can include extending in the respective direction when the sequence identify ratio is higher than a predetermined value; matching base pairs according to the base paring rule; and adding short gaps as necessary to improve the sequence identify ratio and allow for deletion and insertion of nucleotides. The criterion can include stopping the extension when there is no way of satisfying the rule or when the region is longer than a pre-determined length.

In a further aspect, the invention features a method for identifying a microRNA precursor related to a specific biological sample. The method includes (a) taking as input the test value $\text{DIFF}_{CDRs}$ and $\text{DIFF}_{5'UTRs}$ determined by the method and target sections identified by the methods described above, and generating a set of features from said test motifs and values and a characteristic property of said target sections; (b) selecting a set of significant features from said set of features by a procedure based on information theory; (c) applying a machine learning procedure to facilitate the classification of the test motifs and the microRNA precursors; (d) comparing the target section to a microRNA motif for a set of target genes identified by a method described herein; and (e) determining whether the target section includes a fragment that is identical or complementary to the microRNA motif. The target section is determined to be a specific microRNA precursor if the target section contains a segment that is identical or complementary to the microRNA motif; and the target section is determined to be a non-specific microRNA precursor if the target section contains no segment that is identical or complementary to the microRNA motif. The characteristic property of the target section can be a sequence-based property, a structure-based property, or a domain knowledge-based property. The selecting step can include employing a correlation-based filtering technique. The machine learning procedure can include employing a probabilistic classifier technique, a support vector machine (SVM) technique, a decision tree technique, or a neural network technique. The test motif identified in step (c) contains information specific to a biological sample.

In another aspect, the invention features a computer readable medium including software for effecting the following steps: receiving a set of subject nucleic acid sequences, determining a $\text{DIFF}_{CDRs}$ or $\text{DIFF}_{5'UTRs}$ value for at least on RNA motif in the subject nucleic acid sequences according to a method described herein, and outputting the $\text{DIFF}_{CDRs}$ or $\text{DIFF}_{5'UTRs}$ value.

In a further aspect, the invention features a computer readable medium including software for effecting the following steps receiving a subject DNA sequence, identifying a microRNA precursor based on the subject DNA sequence according to the method described above, and outputting the sequence of the microRNA precursor. The software can further effect comparing the sequence of the microRNA precursor to a microRNA motif for a set of target genes identified by a method described above to identify a segment that is identical or complementary to the microRNA motif. The set of target genes can be expressed in a pre-determined biologic sample, which can be prepared from a tissue (e.g., a brain tissue or a liver tissue) or a cell culture (e.g., a HepG2 cell culture). The software can further effect outputting the sequence of the microRNA precursor that has a segment identical or complementary to the microRNA motif or that has no segment identical or complementary to the microRNA motif.

In yet another example, the invention features a computer-readable medium on which is stored a database capable of configuring a computer to respond to queries based on a record belonging to the database. The record includes a first value that identifies a target gene and a second value that identifies a specific microRNA motif or a non-specific microRNA motif associated with the target gene. The specific microRNA motif or non-specific microRNA motif is obtained by the method described above. The record can include a third value that identifies tissue specificity data associated with the target gene. In one example, the record includes the sequence of each microRNA motifs listed in Table 1 below. The set of target genes can be expressed in a pre-determine biologic sample, which can be prepared from a tissue (e.g., a brain tissue or a liver tissue) or a cell culture (e.g., a HepG2 cell culture). In one embodiment, the set of target genes is determined from the microarray expression profiles provided by the Genomics Institute of the Novartis Research Foundation.

The term "target gene" refers to a gene intended for down-regulation via RNA interference ("RNAi"). The term "RNA interference" or "RNAi" refers generally to a sequence-specific or selective process by which a target molecule (e.g., a target gene, protein or RNA) is downregulated. Within the scope of this invention is utilization of RNAi featuring degradation of RNA molecules (e.g., within a cell). Degradation is catalyzed by a enzymatic, RNA-induced silencing complex (RISC). RNAI occurs in cells naturally to remove foreign RNAs (e.g., viral RNAs). Natural RNAi proceeds via fragments cleaved from free double-stranded RNA, which directs the degradative mechanism. Alternatively, RNAi can be initiated by the hand of man, for example, to silence the expression of target genes.

The term "target protein" refers to a protein intended for downregulation via RNAi. The term "target RNA" refers to a RNA sequence that is recognized by a microRNA via partial antisense complementarity. Examples of a target RNA include, but not limited to, sequences known or believed to be involved in the etiology of a given disease, condition or pathophysiological state, or in the regulation of physiological function. A target RNA may be derived from any living organism, such as a vertebrate, particularly a mammal and more particularly a human, or from a virus, bacterium, fungus, protozoan, parasite or bacteriophage. A target RNA may comprise will type sequences, or, alternatively, mutant or variant sequences, including those with altered stability, activity, or other variant properties, or hybrid sequences to which heterologous sequences have been added. Furthermore, a target RNA can include a RNA sequence that has been chemically modified, such as, for example, by conjugation of biotin, peptides, fluorescent molecules, and the like.

A used herein, the term "microRNA" refers to any type of interfering RNAs, including but not limited to, endogenous microRNAs and artificial microRNAs. Endogenous microRNAs are small RNAs naturally present in the genome which are capable of modulation the productive utilization of mRNA. An artificial microRNA can be any type of RNA sequence, other than endogeneous microRNA, which is capable of modulation the productive utilization of mRNA. For instance, it includes sequences previously identified as siRNA, regardless of the mechanism of down-stream processing of the RNA. A microRNA sequence can be an RNA molecule composed of any one or more of these sequences. MicroRNA sequences have been described in publications such as, Lim, et al., 2003, Genes & Development, 17, 991-1008, Lim et al., 2001, Science 294, 858-861, Lagos-Quintana et al., 2002, Current Biologym 12, 735-739, Lagos-Quinana et al., 2001, Science, 294, 853-857, and Lagos-Quitana et al., 2003, RNA, 9, 175-179, which are incorporated herein by reference. Examples of microRNAs include any RNA that is a fragment of a larger RNA or is a miRNA, siRNA, stRNA, sncRNA, tncRNA, snoRNA, smRNA, snRNA, or other small non-coding RNA. See, e.g., U.S. Patent Applications 20050272923, 20050266552, 20050142581, and 20050075492. A "microRNA precursor" refers to a nucleic acid having a stem-loop structure with a microRNA sequence incorporated therein.

A "stem-loop structure" refers to a nucleic acid having a secondary structure that includes a region of nucleotides which are known or predicted to form double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

The term "partial complementarity" refers to at least a portion of the nucleic acid sequences that are capable of base pairing. For instance, in some embodiments two nucleic acid sequences that have partial complementarity have at least 10 nucleotides that are capable of base pairing. In some instances, at least 15 nucleotides in each sequence are capable of participating in a base pairing interaction with one another. In other instances, the two nucleic acids are perfectly complementary, and thus all nucleotides in each sequence are capable of base pairing with a corresponding nucleotide in the other nucleic acid sequence.

The term "region" refers to a portion of a nucleic acid having at least one identifable sequence, structure, function, or characteristic. Within regions of target nucleic acids are segments. A "segments" refers to a smaller or sub-portion of a region within a nucleic acid.

A "coding region" refers to the region between the translation initiation codon and the translation termination codon, is also a region which may be targeted effectively. It can also refers to a region corresponding to an exon. A 5' untranslated region (5'UTR) refers to the portion of an mRNA in the 5' direction from the translation initiation codon, and thus including nucleotides between the 5' cap site and the translation initiation codon of an mRNA (or corresponding nucleotides on the gene). A 3' untranslated region (3'UTR) refers to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

A "biological sample" refers to a sample obtained from a cell culture or a biological subject, including sample of biological tissue or fluid origin, obtained, reached, or collected in vivo or in situ, that contains or is suspected of containing nucleic acids or polypeptides of interest. A biological sample also includes samples from a region of a biological subject containing precancerous or cancer cells or tissues. Such samples can be, but are not limited to, organs, tissues, fractions and cells isolated from mammals including, humans such as a patient, mice, and rats. A biological sample also may include sections of tissues, for example, frozen sections taken for histologic purposes. A biological sample is typically of an eukaryotic origin, for example, insects, protozoa, birds, fish, reptiles, and preferably a mammal, for example, rat, mouse, cow, dog, guinea pig, or rabbit, and more preferably a primate, for example, a chimpanzee or a human.

The details of one or more embodiments of the invention are set fourth in the accompanying drawings and the description below. Other features, objects, and advantages of the invention will be apparent from the description and drawings, and from the claims.

DETAILED DESCRIPTION

The invention relates to methods that employ bioinformatic techniques to construct a high-throughput computational pipeline. In particular, it relates to genome-wide, sequence-based computational methods for microRNA precursor identification. The microRNAs precursor-identifying methods of this invention are based on nucleotide sequences, secondary structures, and motif enrichment. Since they do not need a pre-established training set, profile, or pattern, the efficiency is fairly high. They are useful for identifying novel microRNAs and their targets.

It is known that a microRNA is transcribed as a precursor RNA that contains an RNA stem loop of approximately 80 nucleotides from which the mature single stranded molecule is excised. MicroRNAs can be subdivided into two groups based on their mechanism of gene regulation. The first class of miRNAs are complementary to their target sequences and direct RNA cleavage (i.e., via RNA interference or RNAi). Prediction of this class of microRNA is possible using sequence similarity searches (Rhoades et al., 2002, Cell, 110, 513-520). The second class of miRNAs, exemplified by *C. elegans* miRNAs lin-4 and let7, match their target sequences imperfectly and do not direct RNA cleavage. This imperfect binding has been shown to allow for bulges, mismatches and non-canonical G:U pairing in the middle of the mRNA target. The lin-4 and let7 miRNAs regulate translation of target mRNAs. Alignment of these microRNAs to their targets requires allowing for gaps of variables lengths at variable positions and sequence mismatches. This makes microRNA prediction a difficult computational task.

It is believed that hundreds of microRNA exist in the human genome. Functions are known for hardly any of these, but they are likely to be involved in most, if not all, areas of cell regulation. The methods of this invention are useful for identifying novel microRNAs and their targets.

Molecular mechanisms by which microRNAs regulate gene expression are currently being clarified, but individual biological functions remain largely unknown. It is believe that temporal and spatial expression of microRNAs play key roles in driving cellular specificity. Methods of this invention can be used to define the spatial expression of microRNAs in animals. Novel miRNAs sequences and their target sequences obtainable by the methods are useful in gene regulation.

Figure 1:
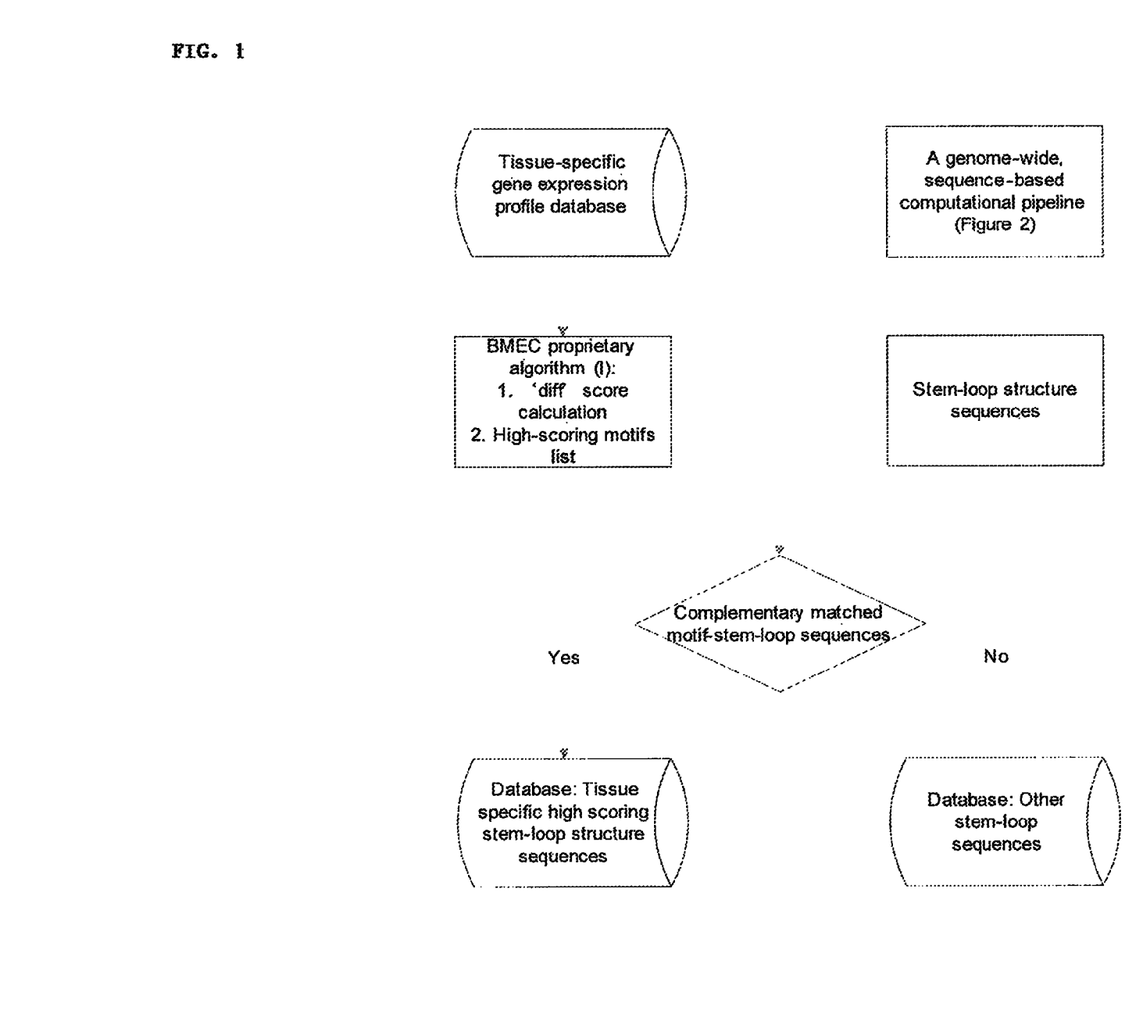
FIG. 1 is a flow chart of an algorithm for identifying microRNA precursors specific or non-specific to a tissue.

Shown in FIG. 1 is a flow chart of a main algorithm, on which is preferred embodiment of this invention is based. The algorithm includes two parts.

Part 1, shown on the upper left side, relates to a BMEC proprietary algorithm for identifying microRNA motifs from one or a set of target genes. It takes the advantage of a so-called 3' UTR-motif enrichment phenomenon in the target sequences of known microRNAs (Lim et al., 2005, Nature, 433, 769~773; and Xie et al., 2005 Nature, 434, 338~345). The BMEC algorithm (I)' scores motifs by the relationship between a motif and microRNAs rather than by the regularly conservation concept. In order to evaluate the 3' UTR enrichment of a motif within a target gene set, a value, named "DIFF" is used to represent the degree of 3' UTR enrichment of a motif. The higher the DIFF of a motif is, the stronger the relationship between the motif and microRNA is. The value "DIFF" is a function of two variables, "OBS" and "EXP." The "OBS" represents the observed count of a motif within a region, such as 5'UTR, CDS or 3' UTR, of a target gene set. The "EXP" represents the expected count of a motif estimated within a region of all gene transcripts. See Functions (I) and (II) above. A preferred embodiment of this invention is based on Formula III and IV shown above. After calculating the DIFF values of all test motifs in a target gene set, one can identify the motifs with higher DIFF values, which are more likely present in microRNA sequences.

These identified motifs can be compared to microRNAs precursors identified by Part II of the above-mentioned main algorithm to identify microRNA presursors that are specific or non-specific for a set of target genes.

Figure 2:
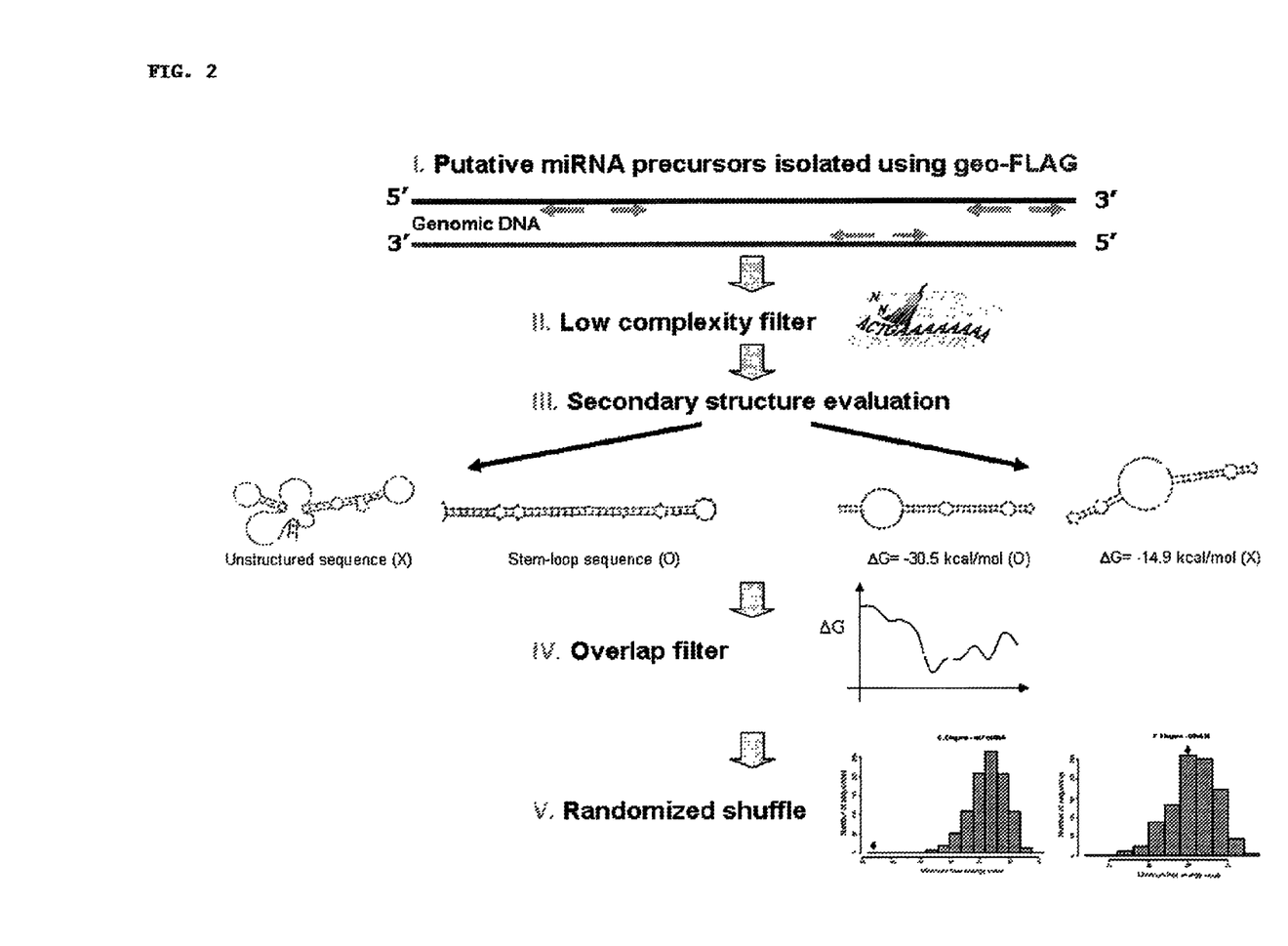
FIG. 2 is a diagram showing steps of a method for identifying microRNA precursors.

Part 2, shown on the upper right side, relates to a computation pipeline that analyzes DNA sequences on the basis of their sequence and structural properties. It allows one to quickly identify microRNAs precursors in a whole genome. This computational pipeline is composed of a cascade of stages or filters. Criterion with increasing stringency is applied as the computation proceeds to the next stage. The pipeline first looks for regions in genomic DNA sequences that have potential to form short hairpins. It then filters out regions that reside in the low complexity regions. Next it examines the thermodynamic properties and secondary structures of retained regions. The candidates are furthered screened according to their geometric shapes. Finally, it uses randomized test to search for the potential precursors with stable secondary structure. This pipeline can be divided into Stages I-V as shown in FIG. 2, which are elaborated on below.

(I) Geo-FLAG

Based on the assumption that functionally important molecules tend to be conserved in sequence and structure across species, several groups have employed comparative genomics approach to detect potential microRNA precursors (Grad et al., 2003, Mol. Cell, 11, 1253-63; Berezikov et al., 2005, Cell, 120, 21-24; and Wang et al., 2005, Bioinformatics, 21, 3610-3614). Known microRNA precursors are collected and used as a training set. The entire genomic DNA sequence are scanned against this set using common sequence alignment tools such as BLAST (Altschul et al., 1997, Nucleic Acids Res., 25, 3389-3402). However, BLAST is not suitable for this task for the following reasons. First, the length (~70 nt) of a typical microRNA precursor is short. Therefore, it is necessary to use a word size much shorter than the default value 11 for BLASTN. Second, extension strategy must be changed to match complementary base pair (including G-T or G-U wobble pairings). Third, substantial efforts are required to post-process the BLAST results to identify possible sequence regions that may form a hairpin structure characteristic of microRNA precursors. Fourth, novel microRNA precursors may be missed simply because they do not "resemble" any known member in the training set.

To facilitate the identification of short hairpins in genomic DNA sequences, we modified a BMEC-proprietary algorithm, FLAG (Fast Local Alignment for Gigabase), a tool for rapid large-scale DNA sequence alignment. This variation of FLAG is called "geo-FLAG." The prefix "geo" stands for geometry, indicating that the FLAG kernel is specially designed for the identification of sequence regions that may form particular geometric shapes, such as a stem-loop or hairpin in our case. Like srnaloop (Grad et al., 2003, Mol. Cell, 11, 1253-63) geo-FLAG adopts the seed-and-extension paradigm. It looks for short complementary words within a specified distance and uses a heuristic method to accelerate the extension. Compared to BLAST, geo-FLAG supports shorter word lengths and aligns complementary base pairs (including G-Us).

(II) Low Complexity Filter

Fragments obtained from the geo-FLAG stage are further filtered to remove those with low complexity. Repeat-masked genomic DNA sequences are downloaded from Ensembl website and compared with the original sequences. In this way, the low complexity regions are identified. All fragments that fall into these regions are discarded. This stage effectively removes more that 60 percent of the candidates.

(III) Secondary Structure Evaluation

The sequence fragments that pass the first two stages have potential to from short hairpins, since they comprise two imperfectly complementary segments within a short range. However, it is necessary to evaluate their thermodynamic properties and RNA secondary structures. For this purposes, Vienna RNA package can be used to examine the minimum free energies of folding and the geometric shapes of these fragments. Sequence fragments that do not form simple hairpins have inappropriate loop sizes or stem lengths, or have unfavorable minimum free energies are discarded.

(IV) Overlap Filter

It is common that geo-FLAG identifies two sequence fragments that overlap with each other significantly. To remove such redundant fragments, overlap filter is applied. Since many microRNA precursors are located in a microRNA cluster (Tanzer et al., 2004, J Mol Biol., 339, 327-335), care should be taken when merging the neighboring fragments so that the potential precursors would not be lost.

(V) Randomized Shuffle

It is known that, in contrast to transfer RNAs and ribosomal RNAs, the great majority of microRNA precursors exhibit a folding energy that is significantly lower than those for shuffled sequences. Accordingly, a randomized test is conducted to screen for the microRNA precursors with highly stable secondary structures. (Bonnet et al., 2004, Bioinformatics, 20, 2911-2917).

In the prediction of RNA secondary structures, contributions from neighboring bases are important to minimum free energy. To assess the stability of the secondary structure, an algorithm that randomly shuffles the sequence while preserving the mono-nucleotide and di-nucleotide frequencies (Workman et al., 1999, Nucleic Acids Res. 27, 4816-4822) can be employed to perform randomized shuffle 1,000 times for each microRNA precursor candidates. The probability p that shuffled sequences have lower energy of folding is calculated. Only those candidates with sequence composition that give rise to very small p (e.g., $\leq 0.005$) or stable secondary structure are retained.

The microRNA motifs and microRNAs precursors respectively identified by Parts 1 and 2 are compared identify microRNA precursors that are specific or non-specific for a target gene or a set of target genes. This step is referred as Stage (VI) and shown on the lower part of FIG. 1. A microRNAs precursor is determined to be specific for the set of target genes if it contains a segment that is identified or complementary to the microRNA motif. Otherwise, it is determined to be a non-specific microRNA precursor for the target gene or the set of target genes. The sequences of each groups of microRNAs precursors thus-identified can be stored on one or more computer readable media to generate databases.

The invention can be implemented in digital electronic circuitry, or in computer hardware, firmware, software, or in combination thereof. Apparatus of the invention can be implemented in a computer program product tangibly embodied in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in ay case, the language can be a compiled or interpreted language. Suitable processors include, by way of example, both general and special purpose microprocessors. Generally, a processor receives instructions and data from a read-only memory and/or a random access memory. A computer can include one or more storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

In addition, the present invention provides a system having a computer, one or more databases containing the cataloged microRNAs precursors or microRNA motif sequences, and a communication link connecting the computer to the one or more databases. The computer is used to select one or more tissue expression or genomic characteristics, select a target gene that is related to the selected characteristics, compare the genomic sequence of the selected gene sequence to the cataloged microRNAs precursor or microRNA motif sequences, extract any cataloged microRNAs precursor or microRNA motif sequences that contain a portion of or match to the genomic gene sequence, align the selected genomic sequence to each extracted microRNAs precursor or microRNA motif sequence, output the extracted sequence. In this system, data (e.g., genomic sequences, tissue-specific gene expression profiles, or cataloged microRNAs precursor or microRNA motif sequences) may be input by downloading from a local site such as a memory or a disk drive, or alternatively from a remote site over a network such as the Internet. The sequences may also be input by keyboard, if necessary.

The microRNAs precursors identified by methods of this invention can be used to regulate the expression of corresponding target genes and develop therapeutics. Depending on functions of a target gene, matching microRNAs precursors can be used treat disorders caused by or associated with abnormal higher level of the target gene. Techniques for making a microRNA-based therapeutic agent and delivering it to a subject in need thereof are known in the art. See, e.g., WO 2005/017111, WO 2004/066183, and U.S. Patent Application 20050186589.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE

The above-described method was used to identity microRNA precursors using the sequences of the plus strands of human chromosomes 19 and 22. MicroRNA reference sets and gene sequences were obtained from the following databases: miRBase v7.0, miRNA expression data from GEO (GSE2564), Ensembl Human genomic DNA database v33 (NCBI build 35.1), NCBI RefSeq database, and GNF SymAtlas v1.1.1.

In Part 1 of the main algorithm, the gene set of whole GNF brain database was processed to identify brain-specific microRNA motifs. A serial of 6-mer motifs were selected. Motifs having both "$DIFF_{CDS}$" and "$DIFF_{5'UTR}$" of greater than 0 were retained. Some of these retained motifs are shown in Table 1 below. The "diff_sum" shown in Table 1 is the summary of $DIFF_{CDS}$ and $DIFF_{5'UTR}$. Remarkable, found in Table 1 is a motif (ccuuaa) that has a diff_sum value of 4.3302 and is related to a known brain microRNA, hsa-mir-124a.

To verify the reliability of the selected motifs (algorithm-selected motifs), a set of 6-mer motifs were randomly selected (randomly-selected motifs). The distribution of microRNAs matching the algorithm-selected motifs or randomly-selected motifs was plotted against the matching mature microRNAs' positions from 5' end to 3' end ("microRNA count vs. the microRNA mature position matching 6-mer motif.").

It was found that algorithm-selected motifs match known microRNAs on their 5' side more than on the 3' side. In other words, the matching positions are more concentrated on the 5' side. In contrast, randomly-selected motifs match mature microRNAs more evenly along the microRNAs. These results are consistent with the result described in Xie et al., 2005, Nature, 434, 338-345, demonstrating that the algorithm-selected motifs are valid.

TABLE 1

| Motifs | Diff_sum | miRNew(Brain, GNF) |
|---|---|---|
| uuuuuu | 5.8886 | New |
| uuaauu | 5.6921 | New |
| uaggua | 5.6912 | New |
| uuuuua | 5.6475 | New |
| uaauuu | 5.6029 | New |
| guuuuu | 5.5834 | New |
| uauaua | 5.5729 | New |
| uguuuu | 5.5553 | New |
| uuuuaa | 5.5223 | hsa-miR-103a |
| uaugua | 5.5167 | New |
| uuguuu | 5.5005 | New |
| uuuugu | 5.4744 | hsa-miR-153 |
| uauuuu | 5.4718 | New |
| uuugu | 5.4683 | New |
| uuuaau | 5.4231 | New |
| uuauuu | 5.4048 | New |
| uaaauu | 5.4046 | New |
| uuugua | 5.3919 | hsa-miR-193 |
| uaguuu | 5.3861 | New |
| uuaagu | 5.3860 | New |
| uuuaaa | 5.3796 | New |
| guauag | 5.3685 | New |
| guaaau | 5.3640 | New |
| uaauac | 5.3543 | New |
| uaguua | 5.3518 | New |
| uguaua | 5.3509 | New |
| uaaaau | 5.3495 | New |
| uuaguu | 5.3471 | New |
| auauau | 5.3330 | New |
| uuuuau | 5.3259 | New |
| cuuuuu | 5.2886 | New |
| uaaguu | 5.2766 | New |
| uuguau | 5.2756 | New |
| uguauu | 5.2706 | New |
| uaauua | 5.2586 | New |
| uuaaaa | 5.2530 | New |
| uauauu | 5.2488 | New |
| auuuuu | 5.2451 | New |
| uauuua | 5.2393 | hsa-miR-16 |
| uuuagu | 5.2372 | New |
| uuuuag | 5.2238 | New |
| uuuuuc | 5.2213 | New |
| auaguu | 5.2089 | New |
| uuaaau | 5.2075 | New |
| uuguaa | 5.2032 | New |

TABLE 1-continued

| Motifs | Diff_sum | miRNew(Brain, GNF) |
|---|---|---|
| uaguau | 5.2021 | New |
| auuucu | 4.4686 | hsa-miR-195 |
| gugugu | 4.4681 | New |
| cuuguu | 4.4662 | New |
| uuuugc | 4.4621 | hsa-miR-19a, hsa-miR-19b |
| uagcau | 4.4616 | New |
| gauuuu | 4.4615 | New |
| uuguug | 4.4578 | New |
| uaacug | 4.4568 | New |
| guauug | 4.4552 | New |
| guaguu | 4.4549 | New |
| ucuguu | 4.4508 | New |
| uaaauc | 4.4491 | New |
| uuauac | 4.4469 | New |
| uugcau | 4.4450 | hsa-miR-19a, hsa-miR-19b |
| uuagcu | 4.4435 | New |
| cuuaac | 4.4420 | New |
| uucaua | 4.4420 | New |
| augugu | 4.4418 | New |
| cuguaa | 4.4413 | hsa-miR-106a, hsa-miR-17-5p |
| uuaaga | 4.4362 | New |
| acuaac | 4.4361 | New |
| uuuagc | 4.4354 | New |
| gcuuuu | 4.4333 | hsa-miR-320 |
| uuuuga | 4.4303 | New |
| uuacuu | 4.4218 | hsa-miR-26a, hsa-miR-26b_(sub_1) |
| uguaca | 4.4149 | hsa-let7g, hsa-miR-103, hsa-miR-107 |
| uaucuu | 4.4148 | New |
| aauuug | 4.4140 | New |
| cuaggu | 4.4122 | New |
| ugcaua | 4.4106 | hsa-miR-19a |
| guaagc | 4.4098 | hsa-miR-106a, hsa-miR-17-5p |
| acugua | 4.4054 | hsa-let-7g, hsa-miR-101, hsa-miR-106a, hsa-miR-139, hsa-miR-17-5p |
| aauaau | 4.4053 | hsa-miR-126* |
| aaaugu | 4.4052 | New |
| auuaac | 4.3966 | New |
| aacuaa | 4.3958 | New |
| ugcuuu | 4.3937 | New |
| acuagu | 4.3892 | hsa-miR-224, hsa-miR-7 |
| cauuua | 4.3854 | New |
| aguuau | 4.3843 | hsa-miR-101 |
| guuaua | 4.3792 | New |
| ucuuau | 4.3787 | New |
| acuugu | 4.3787 | New |
| uacugu | 4.3781 | hsa-miR-101 |
| uauuuc | 4.3772 | hsa-miR-195 |
| aacuuu | 4.3686 | New |
| uguacu | 4.3660 | New |
| acuuua | 4.3636 | hsa-miR-20_(sub_1) |
| cuauau | 4.3630 | New |
| aguuua | 4.3629 | New |
| uaucua | 4.3621 | hsa-miR-9* |
| ugcuuu | 4.3605 | New |
| auguua | 4.3555 | New |
| uguuau | 4.3526 | New |
| uuuccu | 4.3510 | New |
| acauau | 4.3502 | New |
| ucuagu | 4.3477 | New |
| ugcauu | 4.3441 | New |
| cuuagu | 4.3426 | New |
| cauagu | 4.3408 | New |
| cuuuau | 4.3398 | New |
| auaacu | 4.3383 | New |
| acuuag | 4.3366 | hsa-miR-27a, hsa-miR-27b |
| uugagu | 4.3315 | New |
| ccuuaa | 4.3304 | hsa-miR-124a |
| uaggcu | 4.3301 | New |
| uaaaac | 4.3299 | hsa-miR-140 |
| cuaagu | 4.3288 | New |
| gucuua | 4.3251 | New |
| agugua | 4.3231 | hsa-miR-30b, hsa-miR-30c |

TABLE 1-continued

| Motifs | Diff_sum | miRNew(Brain, GNF) |
|---|---|---|
| caugua | 4.3229 | New |
| auguag | 4.3226 | hsa-miR-221 |
| auauug | 4.3205 | New |
| uacauu | 4.3171 | hsa-miR-1 |
| acuauu | 4.3170 | hsa-miR-301 |
| ugcuua | 4.3170 | New |
| uagaaa | 4.3162 | New |
| uuggua | 4.3147 | New |
| acuaaa | 4.3109 | New |
| aaauag | 4.3105 | New |
| uaauuc | 4.3085 | New |
| ucuaua | 4.3079 | New |
| ucuauu | 4.3072 | New |
| uuccuu | 4.3070 | New |
| uugaua | 4.3054 | New |
| auaggg | 4.3029 | hsa-miR-140 |
| cauuaa | 4.3023 | New |
| uuaucu | 4.3023 | hsa-miR-9* |
| uguuuc | 4.3002 | New |
| uuuaca | 4.2999 | hsa-miR-1, hsa-miR-30a*, hsa-miR-30b, hsa-miR-30c, hsa-miR-30d, hsa-miR- |

In Part 2 of the main algorithm, on the average, one million bases were processed per minute at stage 1. The result is shown in Table 2.

TABLE 2

| | | Chromosome | | | | | |
|---|---|---|---|---|---|---|---|
| | | 19 (+), 83.8 MB | | | 22 (+), 49.5 MB | | |
| Step | Criteria | Candidate number | Percentage | Found/Known | Candidate number | Percentage | Found/Known |
| I geo-FLAG | Hairpin | 706.509 | 100.00% | 5/6 | 467.627 | 100.00% | 3/3 |
| II Low complexity | Non-repeat sequences | 278.160 | 39.43% | 5/5 | 196.269 | 44.85% | 3/3 |
| III Secondary structure evaluation | 1 loop <20 and stem >20  2 ΔG ≦ −25 kca/mol | 39.530 | 5.60% | 4/5 | 20.628 | 4.76% | 3/3 |
| IV Overlap | Minimum tree energy | 38.980 | 6.53% | 4/5 | 20.712 | 4.73% | 3/3 |
| IV Randomized shuffle | p ≦ 0.005 | 6.330 | 0.80% | 4/5 | 9.616 | 0.63% | 3/3 |
| VI motif | High Scoring 6-mers IIst | 4.811 | 0.68% | 4/5 | 2.722 | 0.62% | 3/3 |

As shown in Table 2, the pipeline (stages I-V) eliminated more than 99 percent of candidates and identified 4811 candidate microRNA precursors from the initial pool of 705,509 candidates, while 4 out 5 known microRNA precursors were retained ("Found/Known") for human chromosome 19, demonstrating a high sensitivity and a high specificity. These results suggest the present of significantly higher numbers of miRNAs in the human genome than previously estimated.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A computer system for identifying a microRNA precursor, comprising:
   one or more processors configured to execute program instructions; and
   a computer-readable medium containing executable instructions that, when executed by the one or more processors, cause the computer system to perform a method for identifying a microRNA precursor, the method comprising:
   (a) providing a subject DNA sequence;
   (b) searching, by a heuristic algorithm, in the subject DNA sequence of step (a) for a DNA region that has a strong tendency to form a stem loop;
   (c) retaining a DNA region of step (b) that does not reside in a low complexity region of the subject DNA sequence of step (a);
   (d) assessing the ability of the retained DNA region of step (c) to fold into a secondary structure, and selecting a DNA region whose corresponding RNA sequence has a low energy of folding and forms a stem loop;
   (e) comparing the energy of folding of two selected DNA regions of step (d) that overlap with each other substantially such that both overlap ratios exceed a predetermined value, and choosing the one with the lowest energy of folding;
   (f) assessing the stability of a chosen DNA regions of step (e) by performing randomized shuffle of the chosen DNA region a number of times, while keeping a characteristic property of the chosen DNA region unchanged, and calculating a score as a measure of the stability of the secondary structure formed by the chosen DNA region; and
   (g) identifying, from one or more chosen DNA regions, a target section that has a stability score higher than a pre-determined value;
   whereby the target section is determined to be a microRNA precursor.

2. The method of claim 1, wherein the subject DNA sequence is a genomic DNA sequence.

3. The method of claim 1, wherein the heuristic algorithm in step (b) further comprises:
   (1) selecting a pair of seeds that are spaced within a pre-determined distance, wherein the bases of the seeds match to each other according to a base pairing rule; and (2) extending, from said pair of seed of (1), the DNA region in the direction toward and away from each other using an extension rule, and stopping the extension upon the fulfillment of a criterion.

4. The method of claim 1, wherein the low complexity region in step (c) is a region of biased composition including homo-polymeric runs, short-period repeats, or overrepresentation of one or more nucleotides.

5. The method of claim 1, wherein the low energy of folding in step (d) is no greater than −18 kcal/mol.

6. The method of claim 1, wherein the characteristic property of the DNA region in step (f) is a mono-nucleotide distribution or a di-nucleotide distribution.

7. The method of claim 3, wherein the pair of seeds in step (1) are two contiguous segments, each having a length of 3 to 8 nucleotides.

8. The method of claim 3, wherein the base pairing rule in step (1) comprises:
   matching Watson-Crick complementary base pairs (A-T, T-A, C-G, and G-C); and
   matching non-canonical G-T wobble base pairs (G-T and T-G).

9. The method of claim 3, wherein the extension rule in step (2) comprises:
   extending in the respective direction when the sequence identity ratio is higher than a pre-determined value;
   matching base pairs according to the base paring rule; and
   adding short gaps as necessary to improve the sequence identity ratio and allow for deletion and insertion of nucleotides.

10. The method of claim 3, wherein the criterion in step (2) further comprises stopping the extension when there is no way of satisfying the rule or stopping the extension when the region is longer than a pre-determined length.

11. The method of claim 1, wherein the subject DNA sequence contains a genomic DNA sequence from a metazoan species.

12. The method of claim 11, wherein the metazoan species is *Homo Sapiens*.

13. A computer program product, comprising a tangible computer readable medium comprising executable instructions for effecting the following steps:
   (a) receiving a subject DNA sequence;
   (b) searching, by a heuristic algorithm, in the subject DNA sequence for a DNA region that has a strong tendency to form a stem loop;
   (c) retaining a DNA region of step (b) that does not reside in a low complexity region of the subject DNA sequence;
   (d) assessing the ability of the retained DNA region of step (c) to fold into a secondary structure, and selecting a DNA region whose corresponding RNA sequence has a low energy of folding and forms a stem loop;
   (e) comparing the energy of folding of two selected DNA regions of step (d) that overlap with each other substantially such that both overlap ratios exceed a predetermined value, and choosing the one with the lowest energy of folding;
   (f) assessing the stability of a chosen DNA regions of step (e) by performing randomized shuffle of the chosen DNA region a number of times, while keeping a characteristic property of the chosen DNA region unchanged, and calculating a score as a measure of the stability of the secondary structure formed by the chosen DNA region;
   (g) identifying, from one or more chosen DNA regions, a target section that has a stability score higher than a pre-determined value,
   whereby the target section is determined to be a microRNA precursor; and
   outputting the sequence of the microRNA precursor.

14. The computer program product of claim 13, wherein the executable instructions further effect comparing the sequence of the microRNA precursor to a previously identified microRNA motif for a pre-determined set of target genes to identify a segment that is identical or complementary to the previously identified microRNA motif.

15. The computer program product of claim 14, wherein the pre-determined set of target genes are expressed in a pre-determined biological sample.

16. The computer program product of claim 15, wherein the biological sample is obtained from a tissue or a cell culture.

17. The computer program product of claim 14, wherein the executable instructions further effect outputting the sequence of the microRNA precursor that has a segment identical or complementary to the previously identified microRNA motif or that has no segment identical or complementary to the previously identified microRNA motif.

* * * * *

UNITED STATES PATENT AND TRADEMARK OFFICE
CERTIFICATE OF CORRECTION

| | | |
|---|---|---|
| PATENT NO. | : 8,014,956 B2 | Page 1 of 1 |
| APPLICATION NO. | : 11/617042 | |
| DATED | : September 6, 2011 | |
| INVENTOR(S) | : Yu-Ching Chang et al. | |

It is certified that error appears in the above-identified patent and that said Letters Patent is hereby corrected as shown below:

In claim 1, column 14, line 48, "a chosen DNA regions" should read
--a chosen DNA region--.

In claim 3, column 15, line 1, "pair of seed" should read --pair of seeds--.

In claim 9, column 15, line 27, "paring" should read --pairing--.

In claim 13, column 15, line 41, "computer readable medium" should read
--computer-readable medium--.

In claim 13, column 16, line 13, "a chosen DNA regions" should read
--a chosen DNA region--.

Signed and Sealed this
Eighth Day of November, 2011

David J. Kappos
*Director of the United States Patent and Trademark Office*